US012746142B2

(12) United States Patent
Solan

(10) Patent No.: US 12,746,142 B2
(45) Date of Patent: Sep. 29, 2026

(54) ORTHOPAEDIC DEVICE

(71) Applicant: Guy Solan, Godalming (GB)

(72) Inventor: Guy Solan, Godalming (GB)

( * ) Notice: Subject to any disclaimer, the term of this patent is extended or adjusted under 35 U.S.C. 154(b) by 247 days.

(21) Appl. No.: 18/029,350

(22) PCT Filed: Oct. 1, 2021

(86) PCT No.: PCT/GB2021/052544
§ 371 (c)(1),
(2) Date: Mar. 30, 2023

(87) PCT Pub. No.: WO2022/069900
PCT Pub. Date: Apr. 7, 2022

(65) Prior Publication Data

US 2023/0381007 A1 Nov. 30, 2023

(30) Foreign Application Priority Data

Oct. 2, 2020 (GB) ...................................... 2015632
Oct. 2, 2020 (GB) ...................................... 2015691

(51) Int. Cl.
*A61F 5/058* (2006.01)
*A61F 5/01* (2006.01)

(52) U.S. Cl.
CPC .......... *A61F 5/0585* (2013.01); *A61F 5/0111* (2013.01)

(58) Field of Classification Search
CPC .... A61F 5/0111; A61F 5/0113; A61F 5/0585; A61H 1/0266; A63B 71/1225; A63B 2071/1258; A63B 2071/1275; A63B 2071/1283
See application file for complete search history.

(56) References Cited

U.S. PATENT DOCUMENTS 3,800,789 A * 4/1974 Schloss ................. A61F 5/0585 602/6
5,609,570 A 3/1997 Lamont
5,665,059 A 9/1997 Klearman et al.
5,776,090 A 7/1998 Bergmann et al.
5,897,520 A * 4/1999 Gerig .................... A61F 5/0111 602/65
6,019,741 A * 2/2000 Prieskorn ............. A61F 5/0111 602/5
7,682,325 B2 * 3/2010 Chan ..................... A61F 5/0113 128/882
7,727,174 B2 * 6/2010 Chang ................... A61F 5/0111 602/5
9,248,042 B2 2/2016 Lopez et al.
2007/0142759 A1 6/2007 Slautterback et al.
2008/0294082 A1 11/2008 Chang et al.
(Continued)

FOREIGN PATENT DOCUMENTS

EP 2 110 104 A1 10/2009
EP 2 965 725 A1 1/2016
(Continued)

*Primary Examiner* — Keri J Nelson
(74) *Attorney, Agent, or Firm* — BakerHostetler

(57) ABSTRACT

An orthopaedic device, the device includes a splint and attachment means for removably securing the splint to a user's foot and lower leg, wherein the splint is configured such that in use, the user's foot and leg are maintained at an obtuse angle to one another and relative movement between the foot and the leg is substantially prevented.

20 Claims, 7 Drawing Sheets

(56) References Cited

U.S. PATENT DOCUMENTS

| | | | |
|---|---|---|---|
| 2016/0213505 | A1 | 7/2016 | Lopez et al. |
| 2016/0338868 | A1* | 11/2016 | Grimes .................. A61F 5/042 |

FOREIGN PATENT DOCUMENTS

| | | | |
|---|---|---|---|
| GB | 2 167 964 | A | 6/1986 |
| GB | 2 485 454 | A | 5/2012 |
| RU | 2 140 230 | C1 | 10/1999 |

* cited by examiner

ORTHOPAEDIC DEVICE

CROSS-REFERENCE TO RELATED APPLICATIONS

This application is a National Stage of International patent application PCT/GB2021/052544, filed on Oct. 1, 2021, which claims priority to foreign Great Britain patent application Nos. GB 2015632.9 and GB 2015691.5, filed on Oct. 2, 2020, the disclosures of which are incorporated by reference in their entireties.

The invention provides an orthopaedic device for use in treatment and rehabilitation of a patient.

After an individual tears their Achilles' tendon, the foot should remain in a plantar flexed (i.e. tip-toe) position for around ten weeks. Typically, a multipurpose orthopaedic boot is used to maintain this position of the foot. These boots are often large, heavy, well insulated and are not water-resistant. The boot must be worn at night and sleeping becomes difficult because the boot is awkward, hot and uncomfortable. Furthermore, when washing, individuals must remove the boot and this leaves their lower leg unsupported and vulnerable to further injury.

It is an object of the present invention to seek to mitigate problems such as these.

According to the invention there is provided an orthopaedic device, the device comprising a splint and attachment means for removably securing the splint to a user's foot and lower leg, wherein the splint is configured such that in use, the user's foot and leg are maintained at an obtuse angle to one another and relative movement between the foot and the leg is substantially prevented.

The device of the invention thus provides a lightweight, comfortable splint. It can comfortably and conveniently be worn in bed at night by a user, instead of a bulky, heavy boot. In addition, the device could potentially be used by a user whilst washing. Advantageously, the device substantially immobilizes the ankle joint of the user, minimising any horizontal and/or vertical movement of the ankle. Advantageously, the device can hold the user's foot in a plantar flexed position to assist in recovery.

Preferably, the splint comprises a leg section and a foot section, the leg section defining a first plane, the foot section defining a second plane, the sections being rigidly joined such that the angle between the planes is obtuse, thereby limiting tension on the healing Achilles' tendon. More preferably, the angle between the planes may be from about 95° to about 155°. Preferably, the leg section and the foot section may be provided as sections of a single, or one-piece splint body which can be easily manufactured and may ensure that the required angle between the sections is maintained, in use.

Preferably, each section of the splint includes a dorsal side and a ventral side, the leg section ventral side being substantially conformed to the shape of a part of the leg of a patient and the foot section ventral side being substantially conformed to the shape of a part of a foot of a patient.

It is preferred that the leg section ventral side of the splint is conformed to the shape of a shin of a patient and the foot section ventral side of the splint is conformed to the shape of the dorsal side of the foot of a patient.

Typically, the leg section ventral side and the foot section ventral side of the splint are cross-sectionally curved.

Preferably, the device comprises a shell which is sufficiently rigid to maintain the desired spatial relationship between the leg and foot and matches the anatomical contours of the shin, ankle and top of the foot. Typically, the shape of the device matches the contours of the foot when the foot of the user is in a plantar flexed position (i.e. tip-toe).

Preferably, the splint includes padding. Typically, the padding is disposed on the ventral side of the leg section and/or the ventral side of the foot section of the splint. In one embodiment, the padding may comprise a rubber material. Typically, the padding is provided beneath the shell. Advantageously, the padding provides comfort for the user.

Preferably, the splint comprises a substantially rigid material, such as a plastics material or a metal such as aluminium.

Preferably the attachment means comprises one or more elongate straps disposed to releasably secure the splint to the user. Preferably, the device comprises a plurality of straps. In one particularly preferred embodiment the device comprises three straps, namely a calf strap, an ankle strap and a foot strap. Providing a strap in each of these positions has been found to provide a secure and stable fixation of the device to the user. Typically, the straps wrap around the lower leg (i.e. calf), ankle and foot of the user.

In one embodiment, the straps are fixedly attached to the splint. In another embodiment, one or more of the straps may be provided as removable and/or separate from the splint. In particular, where there is an ankle strap, the ankle strap may advantageously be provided as removable and/or separate from the splint. This arrangement has been found to be useful in allowing for adjustment of fit of the device.

It is preferred that where one or more of the straps is fixedly attached to the splint, the or each strap extends from an edge of the splint, generally perpendicularly thereto.

Advantageously, where one or more strap is fixedly attached to the splint, the or each strap may be secured to the device such that the point of attachment is located between the shell and the padding. This arrangement provides stability to the device and in particular, to the splint.

Preferably, the straps comprise securing means such that they may affix to themselves once attached to the user. The securing means may be a reversible securing means such as a hook and loop system. In one embodiment, the securing means comprises Velcro® or a similar attachment material. Advantageously, the use of a reversible securing means allows for attachment and/or detachment of the straps.

In one embodiment, where an ankle strap is provided, the ankle strap may comprise an aperture sized and disposed to enable the strap to wrap around the heel of the user. Conveniently, the aperture may be provided in the form of a slit. In another embodiment, a heel cup may be provided on the ankle strap. Preferably, the heel cup comprises an outer frame and a recess to accommodate the heel of a user. In a yet further embodiment, a slit and also a heel cup may be provided. The slit and/or heel cup thus enables the strap to wrap around the heel of the user which increases the stability of the strap and thus assists in securing the device to the foot and leg of the patient.

Preferably, the splint has a shape that conforms to the user's anatomy. In one embodiment, the splint is shaped to conform to the shape of the user's left leg or right leg and/or left foot or right foot.

In one embodiment, the device is adapted to be attached to the user by a bandage.

In one embodiment, the device is adapted to be attached to the user by a sock.

In another embodiment, the device is adapted to be attached to the user by a sleeve. Typically, the sleeve comprises a toeless sock.

Preferably, the device comprises a pouch or pocket. Typically, the pouch or pocket is adapted to receive the splint.

The invention will now be described solely by way of example by a series of embodiments. For the avoidance of doubt, where a feature is described in connection with one embodiment it is expressly part of this disclosure that it is contemplated for use in each and every other embodiment where that is possible. The embodiments are illustrated by the accompanying drawings, in which, FIG. 1 is a front perspective view illustrating a device according to a first embodiment of the invention;

Figure 1:
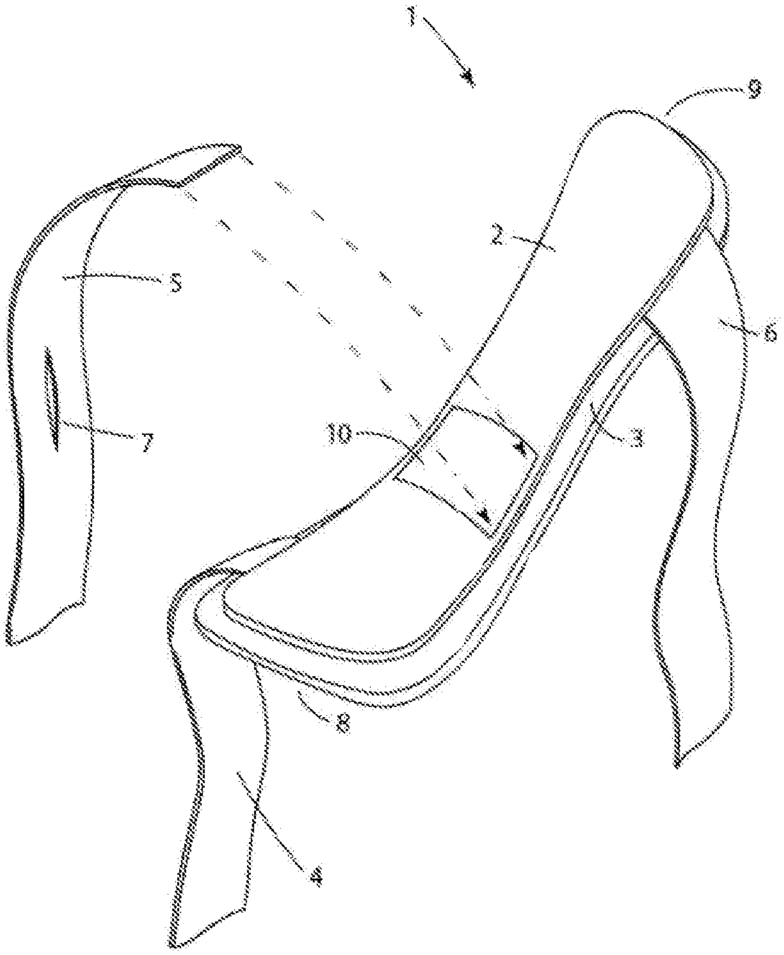

Referring to the drawings, there is provided an orthopaedic device 1 comprising a splint 2 and attachment means 4, 5, 6 for removably securing the splint to a user's foot and lower leg simultaneously, wherein the splint 2 is configured such that in use, the user's foot and lower leg are maintained at an obtuse angle $\alpha$ relative to one another and relative movement between the foot and the lower leg is thereby substantially prevented.

Figure 2:
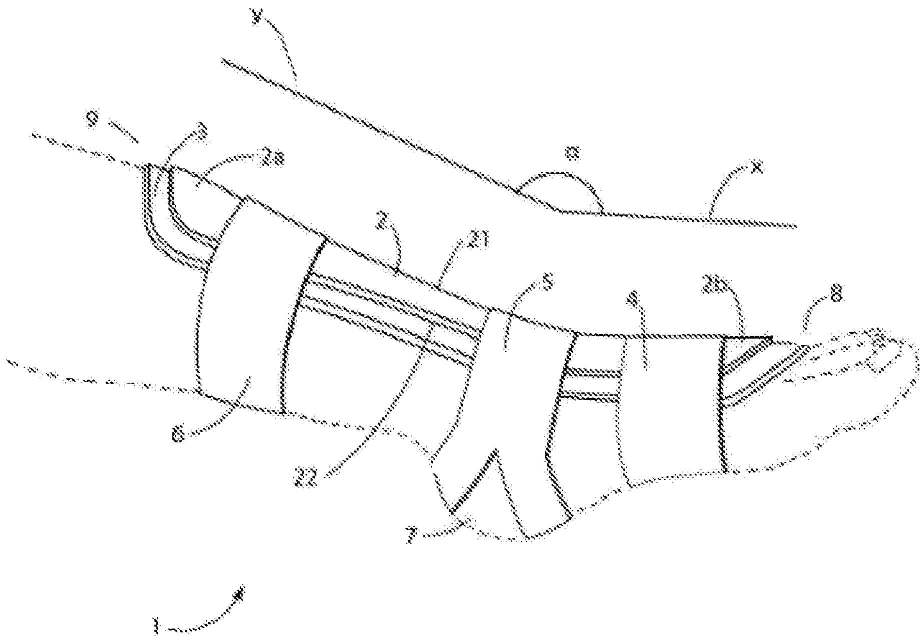
FIG. 2 is a schematic side perspective view of the device of FIG. 1 in use.

Referring to FIG. 2, it can be seen that the splint 2 comprises an elongate, relatively thin body, the body including a leg section 2*a* and a foot section 2*b*. The body is dimensioned such the respective sections will overly the appropriate parts of a user's anatomy and accordingly, different lengths and widths of splint 2 may be specified depending on use. The leg section defines a first plane x, and the foot section defines a second plane y, the sections meeting at a join such that the angle between the planes is from about 95° to about 155°. The join between the sections is rigid such that relative movement between the sections 2*a*, 2*b* is substantially prevented.

The splint 2 includes a dorsal side 21 and a ventral side 22. Both the dorsal and ventral sides have substantially smooth surfaces and are conformed to the shape of the parts of the leg and the foot to which they will be attached. In this embodiment the leg section is conformed to the shape of a shin (left or right) of a patient and the foot section is conformed to the shape of the dorsal side of a foot (left or right) of a patient. As a result, the leg section and the foot section are generally cross-sectionally curved. In addition to being a closer, more comfortable fit to the patient's anatomy, the curved cross section imparts a greater resistance to bending.

The splint 2 can thus be thought of as a rigid shell which matches the anatomical contours of the shin, ankle and top of the foot of the user so that the shape of the device 1 matches the contours when the foot of the user is in a plantar flexed position (i.e. tip-toe). The shape of the rigid shell 2 is comprised of cross-sectional arcs. These arcs become smaller in radius closer to the ankle and much larger in radius where the foot strap 4 is secured. The width of the splint 2 is widest at the posterior edge 9, narrowest at the ankle strap 5, and widens again past the anterior edge 8.

In this embodiment the splint 2 is made from a thermoformable plastics material, in this case polypropylene. Many other thermoplastics would be suitable, including Acrylonitrile Butadiene Styrene (ABS) or High Density Polyethylene (HDPE). It can be made by thermoforming a preformed blank or CNC milling a thermoformed sheet. Injection molding could also produce the part. In other embodiments a light, easily formable metal such as aluminium could be used. Where a thermoformable material is used it is contemplated that to some degree the device could be made bespoke to a particular user's anatomy by utilising a two stage process in which in manufacturing the device is first formed into the correct general shape and then subsequently fitted to the patient by further heating and forming on site by a medical practitioner.

The device 1 includes padding 3 disposed on the ventral side 22 of the leg section and/or the foot section. In the embodiments described here, the padding comprises a sheet of Ethylene-Vinyl Acetate (EVA) foam. In general, any relatively soft, resiliently deformable material can be used, such as Polyethylene (PE) foam or a Polyurethane foam such as memory foam. It is an advantage if the material is water resistant. As can be seen from the Figures, in all embodiments the sheet is sized to be longer and wider than the splint 2. Its thickness is chosen to provide protection to the user from the relatively harder material of the splint 2, especially at its edges, without inhibiting the primary function of the device in immobilising the anatomy.

As mentioned, the device 1 further comprises attachment means, and in the embodiments illustrated in FIGS. 1 to 5, the attachment means comprises three straps 4, 5, 6 disposed to releasably secure the splint to the user. Each strap comprises a length of flexible material, long enough to be passed around the user's anatomy and back upon itself to give an element of adjustability and size accommodation. The material in the illustrated embodiments is woven elastic, however any woven or matted material made from natural or synthetic fibres could be used be it elasticated or not.

With reference to FIG. 1, the foot strap 4 and calf (or leg) strap 6 are fixed to and extend from between the rigid shell 2 and the shell padding 3. In this embodiment, the straps 4 and 6 are permanently fixed in place (for example, the straps are sewn in place).

The ankle strap 5 however, is not permanently fixed in place. Instead a patch 10 of Velcro® or another suitable attachment means is affixed to the dorsal surface of the splint 2. The ankle strap 5 also comprises a patch of Velcro® or another suitable attachment means such that it may be reversibly attached to the splint.

Cut into the ankle strap 5 is an aperture provided by slit 7. The slit 7 enables the strap to wrap around the heel, thus increasing the stability of the strap (as shown in FIG. 2).

FIG. 2 illustrates where the straps should be positioned in relation to the splint when in position on the user's foot and lower leg. The foot strap 4 wraps around the sole of the foot; the ankle strap 5 wraps around the heel; and the calf strap 6 wraps directly below the calf muscle. Each strap wraps around the limb, over the splint 2 and back onto itself where it is secured.

Figure 3:
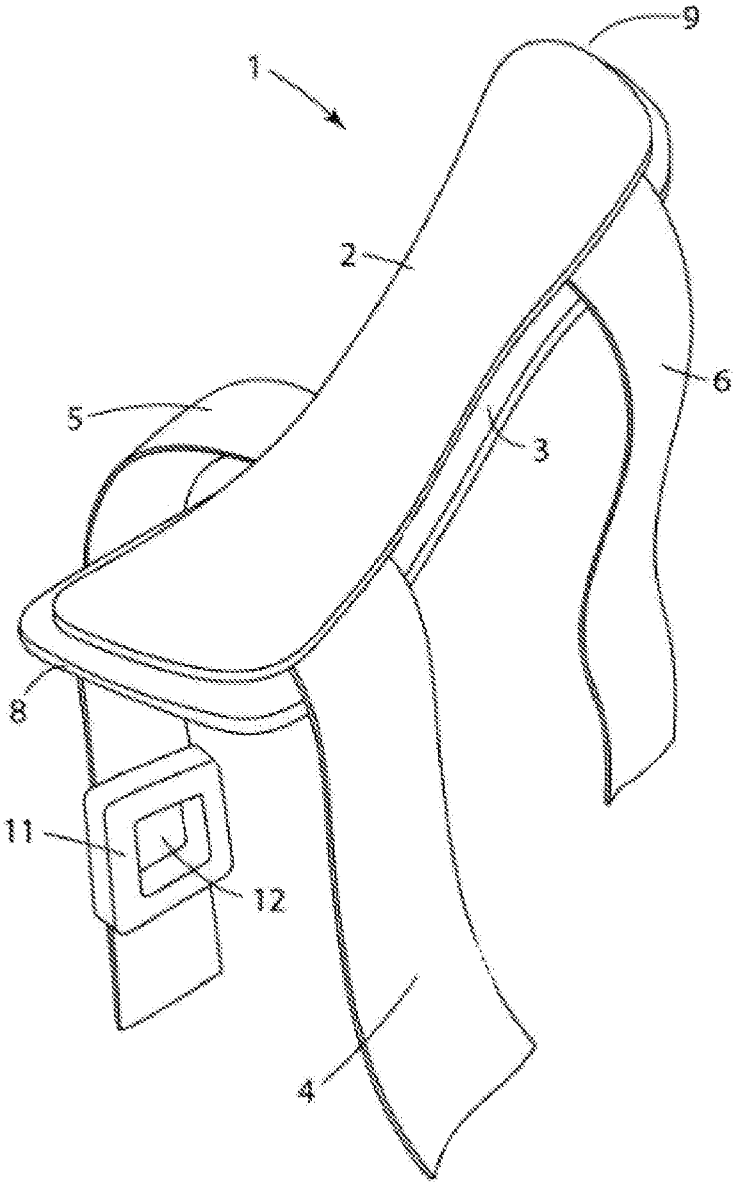
FIG. 3 is a front perspective view of a device according to a second embodiment of the invention.

FIG. 3 illustrates a second embodiment of the invention. In this embodiment, the straps 4, 5, 6 are permanently attached to the rigid shell 2 and shell padding 3 and are sewn in place. The ankle strap 5 comprises a heel cup 12 comprising an outer frame 11 and an inner recess. The heel cup 12 is used to fix the ankle strap 5 in place when wrapped around the ankle of a user (as shown in FIG. 4).

Figure 4:
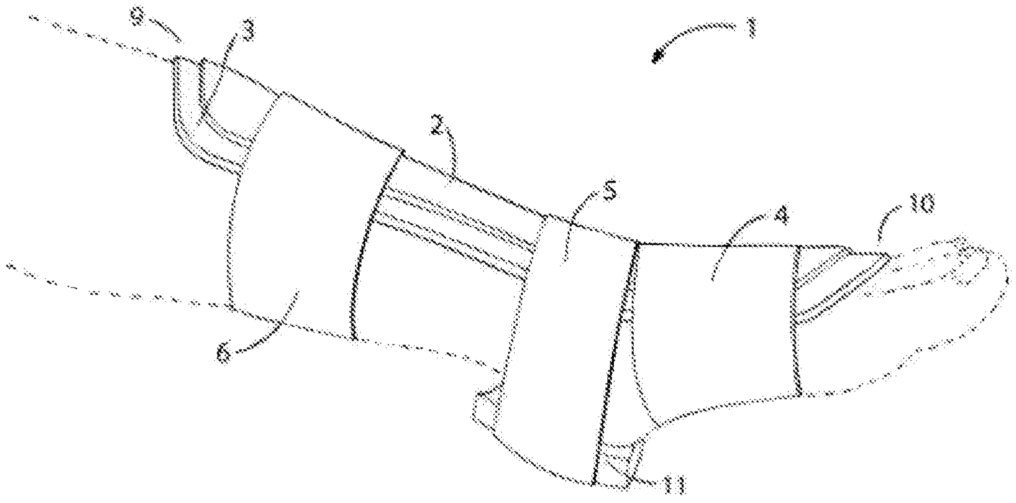
FIG. 4 is a schematic side perspective view of the device of FIG. 3 in use.

FIG. 4 shows the embodiment of FIG. 3 wherein the straps are wrapped around the calf, foot and ankle of the user and the device is held in place.

Figure 5:
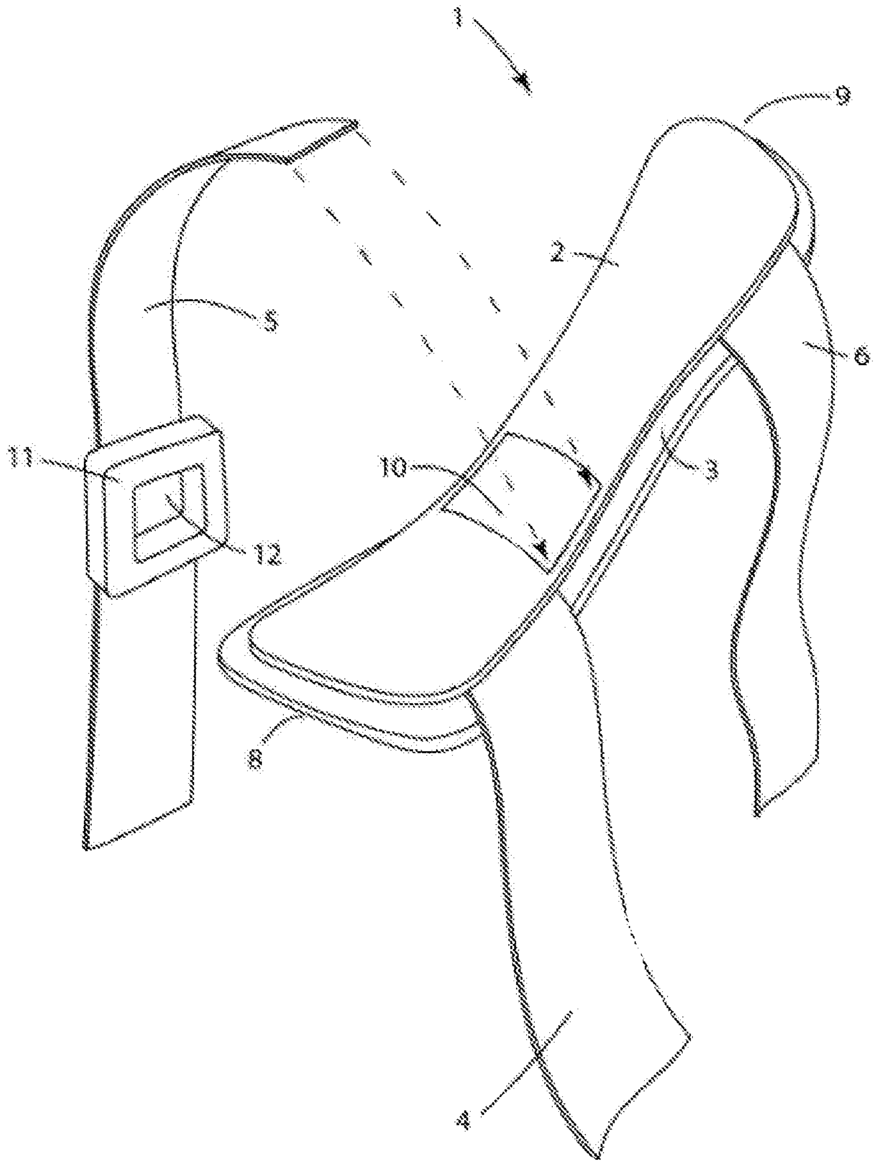
FIG. 5 is a front perspective view of a device according to a third embodiment of the invention.

FIG. 5 shows a third embodiment of the invention. In this embodiment, the ankle strap 5 may be removably attached to the splint by means of Velcro® or another suitable attachment means in a similar way to the embodiment of FIG. 1. In this embodiment, a patch 10 of Velcro® or another suitable attachment means is affixed to the surface of the splint 2. The ankle strap 5 also comprises a patch of Velcro® or another suitable attachment means such that it may be reversibly attached to the splint. The ankle strap 5 comprises a heel cup 12 which is used to fix the ankle strap 5 in place when wrapped around the ankle of a user. In this embodiment, the foot strap 4 and calf strap 6 are permanently attached to the splint.

Figure 6:
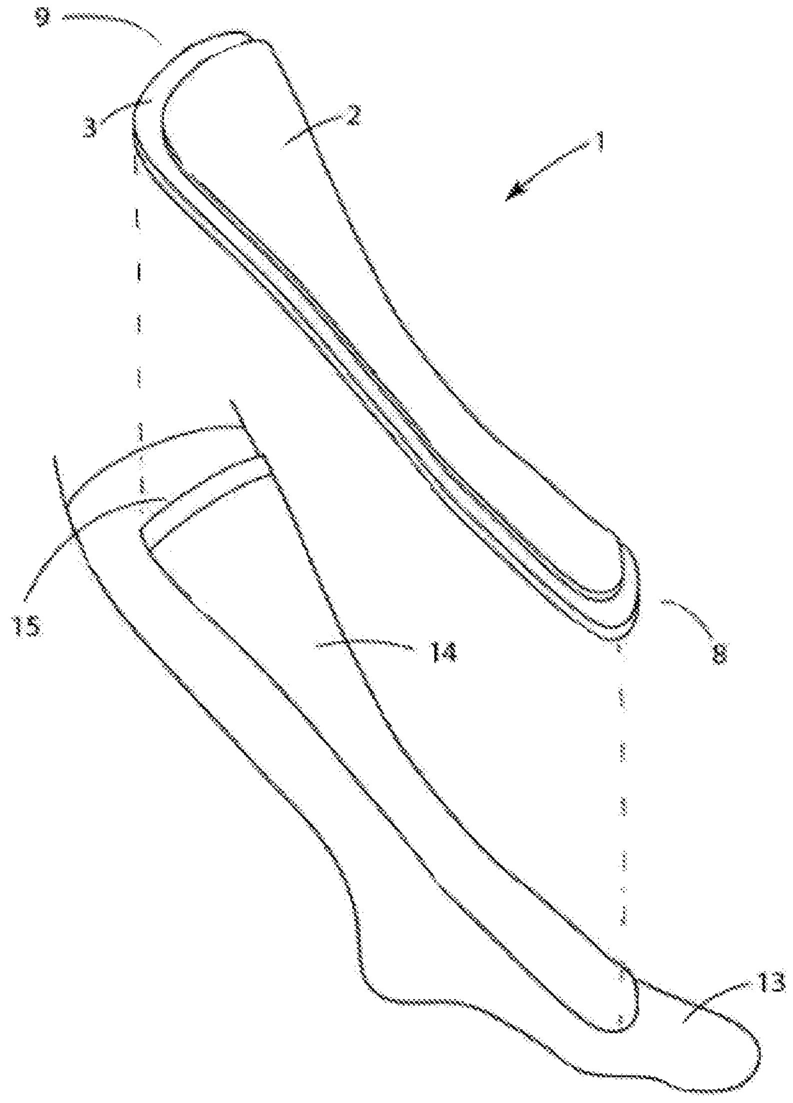
FIGS. 6 and 7 are schematic side perspective views of a device according to fourth embodiment of the invention in an unsecured and secured position, respectively.
Figure 7:
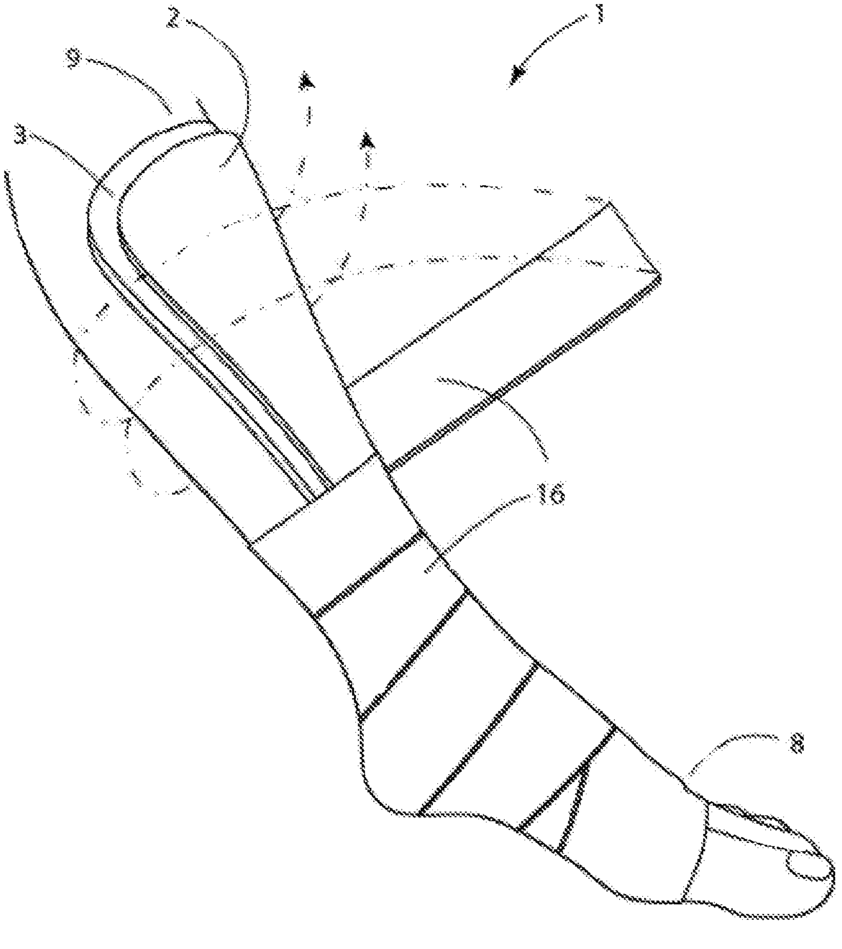

FIGS. 6 and 7 illustrate fourth and fifth embodiments of the invention, respectively, which vary mainly in the nature of the attachment means. Features common to all embodiments have been given common reference numerals to aid in understanding.

Referring to FIG. 6, in this embodiment the splint 2 is provided as described above, however, here the attachment means comprises a sock 13 with a pocket 14 sized to accommodate the splint 2 and positioned to retain it in the optimum position adjacent to the patient's shin and foot. The sock can comprise any known surgical sock or stocking material such as, for example a compression sock.

Referring to FIG. 7, in this embodiment the splint is provided as described above, however, here the attachment means comprises a single strap or bandage 16. The strap or bandage is bound about the splint 2 in place upon the patient's shin and foot, securing it in place and preventing movement.

The invention claimed is:

1. An orthopaedic device, the device comprising a splint and attachment means for removably securing the splint to a user's foot and lower leg, wherein the splint is configured such that in use, the user's foot and leg are maintained at an obtuse angle to one another and relative movement between the foot and the leg is substantially prevented, wherein the splint comprises a leg section and a foot section, the leg section defining a first plane, the foot section defining a second plane, the sections being rigidly joined such that the angle between the planes is from about 95° to about 155°, wherein the leg section and the foot section are sections of a single splint body, each said section including a dorsal side and a ventral side, the leg section ventral side being configured to be substantially conformed to the shape of a part of the leg of a patient and the foot section ventral side being configured to be substantially conformed to the shape of a part of a foot of a user, wherein the leg section ventral side is configured to be conformed to the shape of a shin of a patient and the foot section ventral side is configured to be conformed to the shape of the dorsal side of the foot of a user, wherein the leg section ventral side and the foot section ventral side are cross-sectionally curved.

2. The device according to claim 1, wherein the splint comprises a rigid shell which is configured to match the anatomical contours of the shin, ankle and top of the foot.

3. The device according to claim 1, wherein the splint includes padding.

4. The device according to claim 3, wherein the padding is disposed on a ventral side of the leg section and/or a ventral side of the foot section of the splint.

5. The device according to claim 1, wherein the splint comprises a substantially rigid plastics material.

6. The device according to claim 1, wherein the attachment means comprises a plurality of straps disposed to releasably secure the splint to the user.

7. The device according to claim 6, wherein the plurality of straps comprises a calf strap, an ankle strap and a foot strap.

8. The device according to claim 7, wherein the ankle strap comprises an aperture.

9. The device according to claim 8, wherein the aperture is provided in the form of a slit.

10. The device according to claim 9, wherein the slit enables the ankle strap to wrap around a heel of the user.

11. The device according to claim 7, wherein a heel cup is provided on the ankle strap, wherein the heel cup enables a strap of the plurality of straps to wrap around a heel of the user.

12. The device according to claim 6, wherein the straps comprise securing means such that they may affix to themselves once attached to the user.

13. The device according to claim 1, wherein the device comprises different splints for the user's left and right leg, and/or different sizes of splint in order to match the anatomy of the user.

14. The device according to claim 1, wherein the device is adapted to be attached to the user by a bandage.

15. The device according to claim 1, wherein the device is adapted to be attached to the user by a sock.

16. The device according to claim 15, wherein the sock comprises a pouch.

17. The device according to claim 1, wherein the device is adapted to be attached to the user by a sleeve.

18. An orthopaedic device, the device comprising a splint and attachment means for removably securing the splint to a user's foot and lower leg, wherein the splint is configured such that in use, the user's foot and leg are maintained at an obtuse angle to one another and relative movement between the foot and the leg is substantially prevented, wherein the splint comprises a leg section and a foot section, the leg section defining a first plane, the foot section defining a second plane, the sections being rigidly joined such that the angle between the planes is from about 95° to about 155°, wherein the leg section and the foot section are sections of a single splint body, wherein the splint comprises a rigid shell which is configured to match the anatomical contours of the shin, ankle and top of the foot.

19. An orthopaedic device, the device comprising a splint and attachment means for removably securing the splint to a user's foot and lower leg, wherein the splint is configured such that in use, the user's foot and leg are maintained at an obtuse angle to one another and relative movement between the foot and the leg is substantially prevented, wherein the splint comprises a leg section and a foot section, the leg section defining a first plane, the foot section defining a second plane, the sections being rigidly joined such that the angle between the planes is from about 95° to about 155°, wherein the leg section and the foot section are sections of a single splint body, wherein the splint comprises a substantially rigid plastics material.

20. An orthopaedic device, the device comprising a splint and attachment means for removably securing the splint to a user's foot and lower leg, wherein the splint is configured such that in use, the user's foot and leg are maintained at an obtuse angle to one another and relative movement between the foot and the leg is substantially prevented, wherein the splint comprises a leg section and a foot section, the leg section defining a first plane, the foot section defining a second plane, the sections being rigidly joined such that the angle between the planes is from about 95° to about 155°, wherein the leg section and the foot section are sections of a single splint body, wherein the attachment means comprises a plurality of straps disposed to releasably secure the splint to the user wherein the straps are fixed to be perpendicular to the edge of a rigid shell of the split between said shell and a padding.

* * * * *